United States Patent
Wang

(10) Patent No.: US 11,758,923 B2
(45) Date of Patent: Sep. 19, 2023

(54) METHOD FOR MAKING PLANT-BASED MEATLOAF OR TOFU USING SINGLE CELL PROTEINS FROM MICROALGAE

(71) Applicant: Sophie's BioNutrients Pte. Ltd., Singapore (SG)

(72) Inventor: Yao-Hsin Wang, Singapore (SG)

(*) Notice: Subject to any disclaimer, the term of this patent is extended or adjusted under 35 U.S.C. 154(b) by 0 days.

(21) Appl. No.: 15/930,753

(22) Filed: May 13, 2020

(65) Prior Publication Data

US 2021/0352934 A1    Nov. 18, 2021

(51) Int. Cl.
| A23J 3/34 | (2006.01) |
| A23J 1/00 | (2006.01) |
| A23L 29/00 | (2016.01) |
| C12N 1/12 | (2006.01) |

(52) U.S. Cl.
CPC .............. *A23J 3/347* (2013.01); *A23J 1/008* (2013.01); *A23L 29/065* (2016.08); *C12N 1/12* (2013.01)

(58) Field of Classification Search
CPC .. A23J 3/347; A23J 1/008; A23J 1/009; A23L 29/065; C12N 1/12
USPC .................................................... 426/7
See application file for complete search history.

(56) References Cited

U.S. PATENT DOCUMENTS

| 8,835,142 B2 | 9/2014 | Medoff |
| 2003/0211594 A1 | 11/2003 | Rosebrook |
| 2016/0324167 A1* | 11/2016 | Brooks .................. A23L 15/30 |
| 2017/0137477 A1* | 5/2017 | Patinier .................. C12N 1/12 |
| 2018/0155227 A1 | 6/2018 | Zappi |

FOREIGN PATENT DOCUMENTS

| FR | 3047998 A1 * | 8/2017 | ............. A01G 33/00 |
| WO | 2007134294 A2 | 11/2007 | |
| WO | 2009086307 A1 | 7/2009 | |
| WO | 2015071908 A1 | 5/2015 | |

* cited by examiner

*Primary Examiner* — Hamid R Badr
(74) *Attorney, Agent, or Firm* — Gearhart Law, LLC; David Postolski

(57) ABSTRACT

Methods for making a plant-based food product from a microalgae are described. An example method includes obtaining a microalgae, extracting *Chlorella* protein from the microalgae, modifying a factor associated with the *Chlorella* protein and/or adding a stimulant to the *Chlorella* protein to change an amino acid combination of the *Chlorella* protein, and utilizing the modified *Chlorella* protein as a protein flour to create the plant-based food product.

10 Claims, 5 Drawing Sheets

METHOD FOR MAKING PLANT-BASED MEATLOAF OR TOFU USING SINGLE CELL PROTEINS FROM MICROALGAE

FIELD OF THE EMBODIMENTS

The field of the invention and its embodiments relate to methods for making a plant-based food product from a microalgae. In particular, the present invention introduces methods for modifying amino acid combinations in *Chlorella* protein of the microalgae such that the *Chlorella* protein has similar nutritional and applicational profiles to the animal protein it is trying to replace.

BACKGROUND OF THE EMBODIMENTS

Algae are photosynthetic organisms that grow in a range of aquatic habitats, including lakes, pounds, rivers, and oceans. Algae can tolerate a wide range of temperatures, salinities, and pH values, as well as differing light intensities. Additionally, algae may also grow alone or in symbiosis with other organisms. Algae may be broadly classified as Rhodophyta (red algae), Phaeophyta (brown algae), or Chlorophyta (green algae). Algae may be further classified by size, as macroalgae (which are multicellular, large-size algae that are visible with the naked eye) or microalgae (which are microscopic, single cells that may be prokaryotic or eukaryotic).

Currently, there are an estimated 300,000 to 1 million species of microalgae in existence. Microalgae has recently attracted considerable interest due to their extensive applications in the renewable energy field, the biopharmaceutical field, and the nutraceutical field. Specifically, microalgae may be a sustainable and economical source of biofuels, bioactive medicinal products, and food ingredients. Moreover, microalgae also have applications in wastewater treatment and atmospheric $CO_2$ mitigation. Thus, microalgae produces a wide range of bioproducts, including polysaccharides, lipids, pigments, proteins, vitamins, bioactive compounds, and antioxidants.

*Chlorella* is a genus of single-celled green algae belonging to the division Chlorophyta. *Chlorella* I spherical in shape, about 2 to 10 μm in diameter, and is without flagella. It contains the green photosynthetic pigments chlorophyll-a and -b in its chloroplast. *Chlorella* multiples rapidly, requiring only carbon dioxide, water, sunlight, and a small amount of minerals to reproduce.

*Chlorella* is a potential food source since it is high in protein and other essential nutrients. For example, when dried, *Chlorella* contains about 45% protein, 20% fat, 20% carbohydrate, 5% fiber, and 10% minerals and vitamins (e.g., vitamin B12, vitamin C, iron, magnesium, zinc, copper, potassium, and/or calcium, etc.). Due to this, *Chlorella* has been labeled as a "superfood" and has garnished significant attention from the vegan community. Further, *Chlorella* has been explored as a potential source of food and energy because its photosynthetic efficiency can, in theory, reach 8%, which exceeds that of other highly efficient crops, such as sugar cane.

With increasing attention being paid to the consumption of healthy nutritional foods, algal protein has moved to the forefront of non-animal protein sources. However, the applications of *Chlorella* protein as a functional ingredient in food still requires further exploration.

Thus, a need exists for methods to use *Chlorella* protein in plant-based food products (such as meatloaf and tofu). Moreover, a need exists for methods to modify the amino acid combinations in the *Chlorella* protein such that the *Chlorella* protein has similar nutritional and applicational profiles to the animal protein it is trying to replace.

REVIEW OF RELATED TECHNOLOGY

U.S. Pat. No. 8,835,142 B2 describes a method to process biomass (e.g., plant biomass, animal biomass, microbial, and municipal waste biomass) to produce useful products, such as food products and amino acids.

WO 2015/071908 A1 describes a method to produce microalgae that shows high growth rate under wide conditions, including extreme light intensities.

WO 2007/134294 A2 describes algal species and compositions, as well as methods for identifying algae that produce high lipid content, possess tolerance to high $CO_2$, and/or can grow in wastewater.

U.S. Published Patent Application No. 2003/0211594 A1 describes a novel microalgal strain and progeny thereof, useful for the remediation of waste water.

U.S. Published Patent Application No. 2018/0155227 A1 describes a biorefinery system (BIOSYS) that effectively treats all human activity-derived waste (e.g., black water, grey water, and food waste streams) using biological systems and produces as process by-products: recovered potable water, liberated free oxygen, edible protein cake (with and without lipids), soil amendments, and machinery lube oils.

WO 2009/086307 A1 describes a method for treating biomass waste to result in usable byproducts. Biomass is treated to remove debris, transferred to microbial digester units, such as anaerobic and aerobic digesters, and the resultant solids and liquids are provided to an algae production unit. Algae are harvested and beneficial byproducts are retained. Gases, heat and energy produced by energy conversion units are used in units of the system or provided to external sources. Water is cleaned and when separated from the algae and other solids in the algae harvesting unit may be provided to external sources, or may be used in other units of the system.

CN 105861312 A describes a method for culturing microalgae by adding an anaerobic digestion liquid of kitchen waste into natural seawater, aims to find out the best proportion, and belongs to the technical field of the microalgae. According to the invention, the digestion liquid is added to natural seawater according to the ratio of (1:10)-(1:50) to be taken as an experimental group culture medium, BG11, natural seawater and the digestion liquid are taken as a control group, the experimental group culture medium is cultured under the condition of continuous light until the microalgae stops to grow, and centrifugal separation is carried out to obtain the microalgae. The result shows that the growth rate of the microalgae added with the digestion liquid and cultured in natural seawater is obviously higher than that of the microalgae cultured in the BG 11 and pure seawater, furthermore, natural seawater added with the digestion liquid is taken as the culture medium to improve the lipid yield of the microalgae and lower the cultivation cost of the microalgae, so that the method for culturing the microalgae by adding the anaerobic digestion liquid of the kitchen waste to natural seawater is worthy of being popularized and applied.

KR 101287384 B1 describes a method for cultivating microalgae, which includes cultivating *Botryococcus braunii* in an optical condition mixing LED light with 640 nm wavelengths and 460 nm wavelengths in a ratio of 5:1.

Various methods for making plant-based food products are known in the art. However, their means of operation are substantially different from the present disclosure, as the other inventions fail to solve all the problems taught by the present disclosure. The present invention and its embodiments provide methods for making a plant-based food product from a microalgae. In particular, the present invention introduces methods for modifying amino acid combinations in *Chlorella* protein of the microalgae such that the *Chlorella* protein has similar nutritional and applicational profiles to the animal protein it is trying to replace.

SUMMARY OF THE EMBODIMENTS

The present invention and its embodiments provide methods for making a plant-based food product from a microalgae. In particular, the present invention introduces methods for modifying amino acid combinations in *Chlorella* protein of the microalgae such that the *Chlorella* protein has similar nutritional and applicational profiles to the animal protein it is trying to replace.

A first embodiment of the instant invention describes a method for making a plant-based food product from a microalgae. The method first includes obtaining the microalgae. A strain of the microalgae may include: a *Botryococcus sudeticus* strain, a *Botryococcus* strain, a *Neochloris oleabundans* strain, a *Neochloris* strain, a *Chlamydomonas reinhardtii* strain, or a *Chlamydomonas* strain, among others.

The method further includes extracting *Chlorella* protein from the microalgae. Numerous extraction methods may be used, such as mechanical grinding, high-pressure homogenization, ultrasonic treatment, pulse dyslenoid to release the protein molecules to facilitate further extraction processes like water, alkali or enzyme, and then use of isoelectric precipitation, and salting out (salt induced precipitation) methods. Moreover, other extraction methods may include an alkaline solution extraction method, an enzyme extraction method, and a low-temperature deep eutectic solvents (DES) extraction method, among others.

The alkaline solution extraction method includes adding an alkaline solution to a powder of the microalgae to form a mixture. In some examples, the alkaline solution is added in a range between approximately 0% to approximately 10% of a weight of the *Chlorella* protein. In some examples, the alkaline solution is added in a range between approximately 1% to approximately 8% of the weight of the *Chlorella* protein. In additional examples, the alkaline solution is a sodium hydroxide (NaOH) solution. In other examples, the algae powder comprises a protein content in a range of approximately 30% to approximately 90%. In some examples, the algae powder comprises a protein content in a range of approximately 60% to approximately 65%.

The method further includes extracting the *Chlorella* protein from the mixture at approximately 50° C. for approximately 6 hours and centrifuging the mixture for approximately 20 minutes to obtain a protein extract solution of the *Chlorella* protein. In examples, a protein recovery rate from the protein extract solution of the *Chlorella* protein may be calculated. The protein recovery rate of the protein extract solution is calculated by:

$$\text{Protein recovery rate}/\% \frac{\text{Supernatant protein content} \times \text{supernatant mass}}{\text{Chlorella mass} \times \text{algal powder protein content}} \times 100.$$

The enzyme extraction method includes dissolving a powder of the microalgae in water to form a solution. In some examples, the algae powder is present in approximately 25.0 grams and the water is present in approximately 375 mL. The method may then include adding an alkaline protease to the solution. In examples, the alkaline protease is present in a range of approximately 0.001% to approximately 0.5%. In some examples, the alkaline protease is present in a range of approximately 0.01% to approximately 0.2%. The method may further include adjusting a pH of the solution to the pH of 8.0, hydrolyzing the solution at a temperature of approximately 55° C. with an alkaline solution for approximately 24 hours, and centrifuging the mixture for approximately 20 minutes to obtain a protein extract solution of the *Chlorella* protein. In examples, the method may further include calculating the protein recovery rate from the protein extract solution of the *Chlorella* protein.

The low-temperature DES extraction method may include: adding a first material:a second material having molar ratios of 1:2 to an algae powder:cryogenic co-melt solvent having molar ratios of 1:9 to form a mixture. In a first example, the first material:second material is glycerol:choline chloride. In a second example, the first material:second material is urea:choline chloride. The method may further include reacting the mixture at a temperature of approximately 60° C. for approximately 3 hours and centrifuging the mixture for approximately 20 minutes to obtain a protein extract solution of the *Chlorella* protein. In examples, the method may further include calculating the protein recovery rate from the protein extract solution of the *Chlorella* protein.

The method for making the plant-based food product from the microalgae may further include modifying a factor associated with the *Chlorella* protein and/or adding a stimulant to the *Chlorella* protein to change an amino acid combination of the *Chlorella* protein. In an example, the factor may include a pH level of the microalgae, a wavelength of irradiance of light onto the microalgae during the fermentation process, a feedstock for the microalgae, a carbon source of a culture media in which the microalgae is located, a growth temperature for the microalgae, a flow rate of air into a bioreactor during a fermentation process, a flow rate of air/O2 mixtures into the bioreactor during the fermentation process, a flow rate of noble gases into the bioreactor during the fermentation process, and/or an incubation time period for the microalgae under a mixotrophic growth condition, among others. In additional examples, the stimulant is a substrate and may include a spent grain, okara, or molasses, among other examples. The method may additionally include utilizing the modified *Chlorella* protein as a protein flour to create the plant-based food product. The plant-based food product is a meat loaf or a tofu.

In general, the present invention succeeds in conferring the following benefits and objectives.

It is an object of the present invention to provide methods for making a plant-based food product from a microalgae.

It is an object of the present invention to provide methods for modifying amino acid combinations in *Chlorella* protein of the microalgae such that the *Chlorella* protein has similar nutritional and applicational profiles to the animal protein it is trying to replace.

DESCRIPTION OF THE PREFERRED EMBODIMENTS

Figure 1:
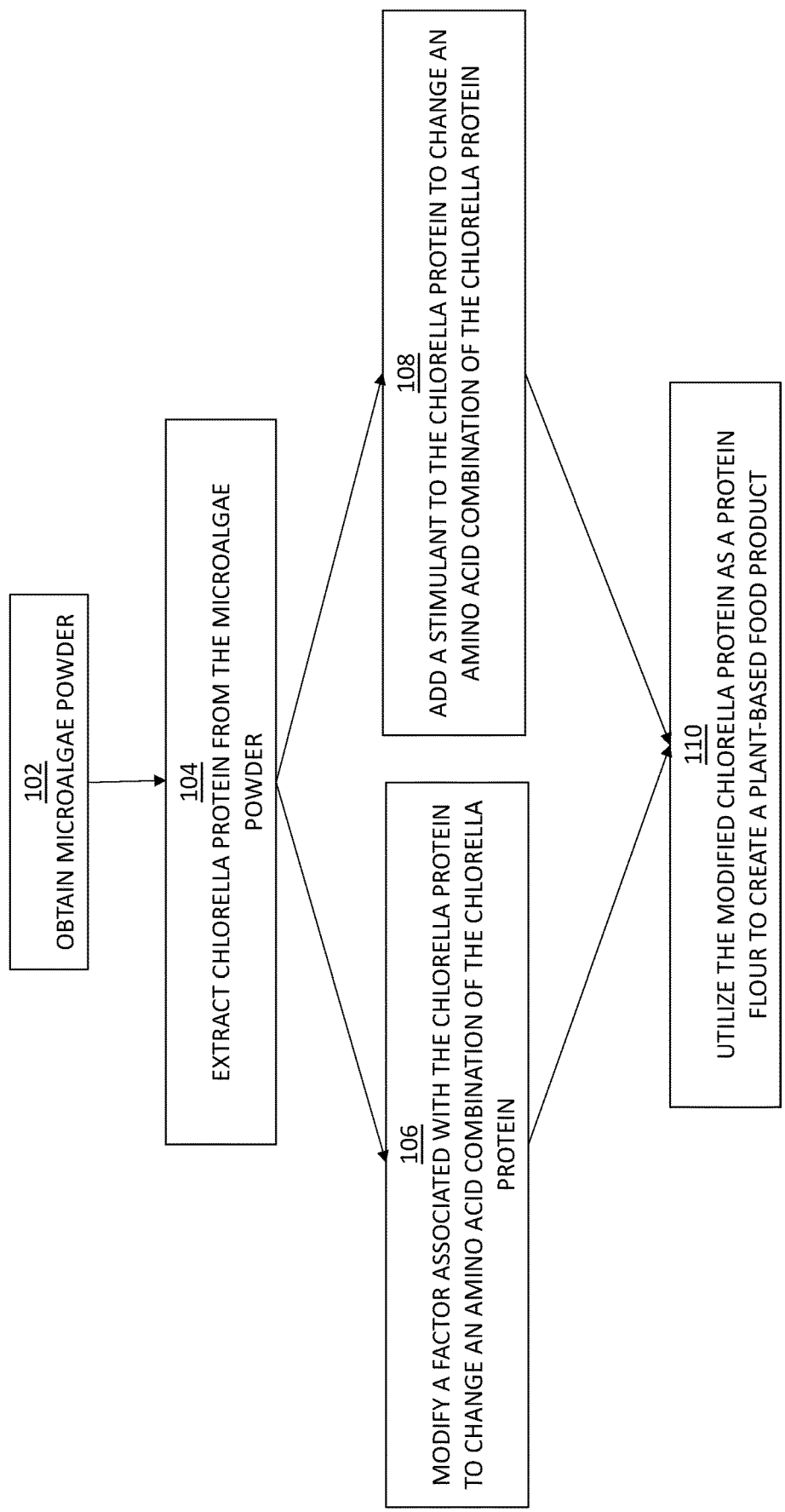
FIG. 1 depicts a schematic block diagram of a method for making a plant-based food product from a microalgae, according to at least some embodiments described herein.

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

As described herein, a "bioreactor" is an enclosure or partial enclosure, in which cells are cultured, and optionally in suspension.

As defined herein, an "autotroph" refers to an organism that is capable of synthesizing its own food from inorganic substances, using light or chemical energy.

As defined herein, a "feed stock" refers to what kind of food waste one uses to feed microalgae. Different feed stocks include differing nitrogen and carbon sources.

As defined herein, a "heterotroph" refers to an organism that cannot synthesize its own food and is dependent on complex organic substances for nutrition.

As defined herein, a "microalgae" refers to a eukaryotic microbial organism that contains a chloroplast, and optionally, that is capable of performing photosynthesis, or a prokaryotic microbial organism capable of performing photosynthesis.

As defined herein, a "mixotrophic strain" is defined as a strain of an organism that allows it to be both autotrophic and heterotrophic at the same time.

FIG. 1 depicts a schematic block diagram of a method for making a plant-based food product from a microalgae, according to at least some embodiments described herein. The method of FIG. 1 may begin at a process step 102, which includes obtaining the microalgae. In some examples, the microalgae may first be cultivated in a bioreactor system (such as a fermentation tank) prior to obtaining the microalgae. A culture media may include a carbon source and may be located inside of the bioreactor system. The microalgae may be located in the culture media.

A strain of the microalgae may include: a *Botryococcus sudeticus* strain, a *Botryococcus* strain, a *Neochloris oleabundans* strain, a *Neochloris* strain, a *Chlamydomonas reinhardtii* strain, or a *Chlamydomonas* strain, among others. In additional examples, the microalgae is of a mixotrophic strain. In examples, the microalgae may be adapted for both autotrophic growth and heterotrophic growth during a time period.

The process step 102 may be followed by a process step 104, which includes extracting *Chlorella* protein from the microalgae. Numerous extraction methods may be used, such as mechanical grinding, high-pressure homogenization, ultrasonic treatment, pulse dyslenoid to release the protein molecules to facilitate further extraction processes like water, alkali or enzyme, and then use of isoelectric precipitation, and salting out (salt induced precipitation) methods. Additional extraction methods include: an alkaline solution extraction method (depicted and described in FIG. 2), an enzyme extraction method (depicted and described in FIG. 3), and a low-temperature DES extraction method (depicted and described in FIG. 4 and FIG. 5), among others. It should be appreciated that further extraction methods may be used, which are not explicitly listed herein.

The process step 104 is followed by a process step 106 and/or a process step 108. The process step 106 includes: modifying a factor associated with the *Chlorella* protein to change an amino acid combination of the *Chlorella* protein. In examples, the factor may include a pH level of the microalgae, a wavelength of irradiance of light onto the microalgae during the fermentation process, a feedstock for the microalgae, a carbon source of the culture media in which the microalgae is located, a growth temperature for the microalgae, a flow rate of air into the bioreactor during a fermentation process, a flow rate of air/$O_2$ mixtures into the bioreactor during the fermentation process, a flow rate of noble gases into the bioreactor during the fermentation process, and/or an incubation time period for the microalgae under the mixotrophic growth condition, among others. In examples, the carbon source for the culture media may be glucose, fructose, sucrose, galactose, xylose, mannose, rhamnose, N-acetylglucosamine, glycerol, floridoside, glucuronic acid, corn starch, depolymerized cellulosic material, sugar cane, sugar beet, lactose, milk whey, or molasses, among other examples not explicitly listed herein. The process step 108 may include adding a stimulant to the *Chlorella* protein to change the amino acid combination of the *Chlorella* protein. In additional examples, the stimulant is a substrate and may include a spent grain, okara, or molasses, among other examples.

It should be appreciated that changing the amino acid combination of the *Chlorella* protein by the process step 106 and/or the process step 108 may result in the creation of functional proteins. Proteins are macromolecules consisting of one or more long chains of amino acid residues. Proteins perform a vast array of functions within organisms, including catalyzing metabolic reactions, DNA replication, responding to stimuli, providing structure to cells, and organisms, and transporting molecules from one location to another. Proteins differ from one another primarily in their sequence of amino acids, which is dictated by the nucleotide sequence of their genes, and which usually results in protein folding into a specific three-dimensional structure that determines its activity.

Amino acids are the basic building blocks of the body and are organic compounds that contain amine (—NH2) and carboxyl (—COOH) functional groups, along with a side chain (R group) specific to each amino acid. In the form of proteins, amino acid residues form the second-largest component (water is the largest) of human muscles and other tissues. Amino acids are extremely versatile and more than 200 different amino acids exist. The most commonly known are the 22 proteinogenic amino acids.

Amino acids prove to be beneficial in numerous fields. Thus, modifying the amino acid combination in the *Chlorella* protein may result in the creation of functional proteins.

The modified *Chlorella* protein may be used as a protein flour with different application functions, different nutritional functions, and/or different functional properties based on the modified factor(s) and/or the applied stimulant(s). Such functional properties performed by proteins in food include: solubility, water absorption and binding, viscosity, gelation, cohesion-adhesion, elasticity, emulsification, fat adsorption, flavor binding, and/or foaming, among others. For example, water absorption and binding may be significant in meats, sausages, breads, and cakes, and may be the result of hydrogen-bonding of water and entrapment of water. Additionally, viscosity may be significant for soups and gravies and may result from thickening. Gelation may be important in meats, curds, and cheeses, and may be a result of protein matrix formation and setting. As such, one can use the modified *Chlorella* protein powder that has similar nutritional, functional, and applicational profiles to the animal protein it is trying to replace.

The process step 106 and/or the process step 108 may be followed by a process step 110, which may include: utilizing the modified *Chlorella* protein as the protein flour to create the plant-based food product. The plant-based food product is a meat loaf or a tofu. It should be appreciated that the modified *Chlorella* protein may be used in multiple food applications not explicitly listed herein.

Figure 2:
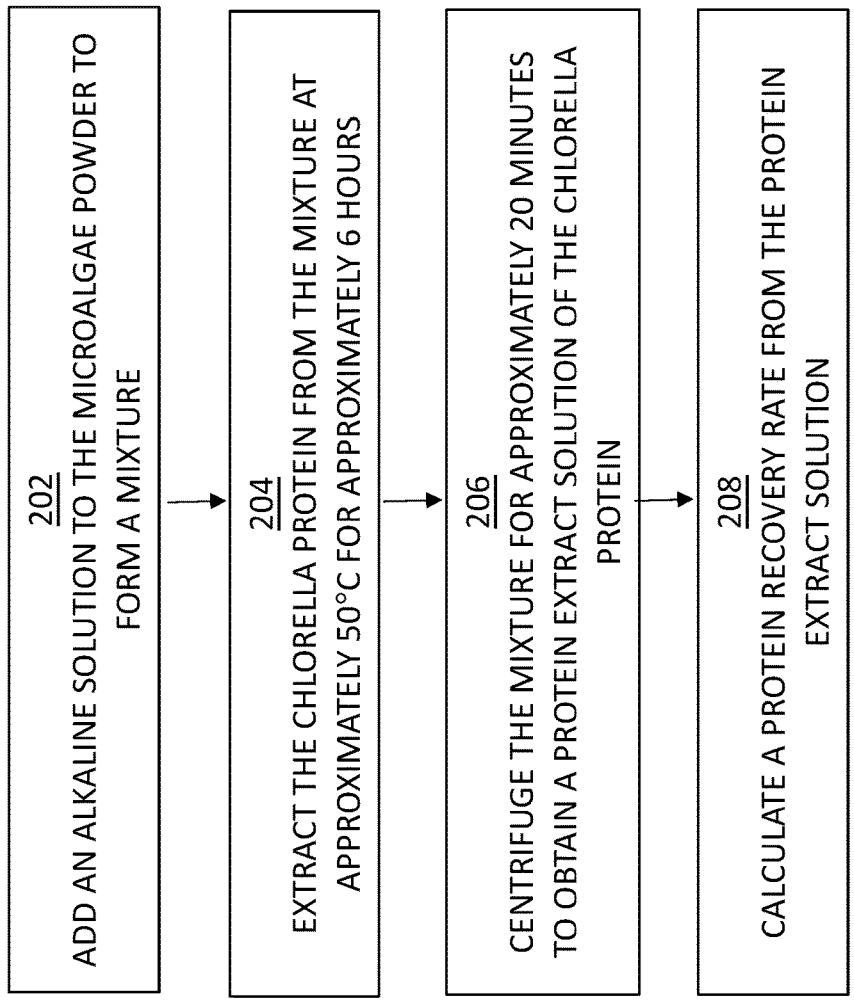
FIG. 2 depicts a schematic block diagram of an alkaline solution extraction method for *Chlorella* protein, according to at least some embodiments described herein.

FIG. 2 depicts a schematic block diagram of an alkaline solution extraction method for *Chlorella* protein, according to at least some embodiments described herein. Since most proteins are acidic, when a protein is near its isoelectric point (PI—4 to 5), solubility will be minimized. For example, in alkaline conditions, proteins will be more soluble. At the same time, alkaline affects the protein molecule's secondary bonds. Hydrogen bonds can have a certain destructive effect and can change the polarity, so that the protein molecular surface charge changes, which modifies the solubility of the protein molecules, which will separate the protein for extraction.

The method of FIG. 2 begins at a process step 202, which includes adding an alkaline solution to the microalgae powder to form a mixture. In some examples, the microalgae powder is a green bao algae powder comprising a protein content in a range of approximately 30% to approximately 90%. In examples, the microalgae powder comprises a protein content in a range of approximately 60% to approximately 65%.

The mass of *Chlorella* may be in a range of approximately 1.0 grams to approximately 10.0 grams. In some examples, the mass of *Chlorella* may be in a range of approximately 5.0 grams to approximately 6.0 grams. In examples, the amount of the alkaline solution is in a range between approximately 0% to approximately 10% of a weight of the *Chlorella* protein. In further examples, the amount of the alkaline solution is in a range between approximately 1% to approximately 8% of a weight of the *Chlorella* protein. In other examples, the alkaline solution is a sodium hydroxide (NaOH) solution.

The process step 202 is followed by a process step 204, where an extraction of the mixture is carried out at approximately 50° C. for approximately 6 hours. The process step 204 is followed by a process step 206, where the mixture is centrifuged at approximately 800 rpm for approximately 20 minutes to obtain a protein extract solution of the *Chlorella* protein. The process step 206 is followed by a process step 208, where a protein recovery rate is calculated from the protein extract solution of the *Chlorella* protein. The protein recovery rate may be calculated by Equation 1 shown below:

$$\text{Protein recovery rate}/\% = \frac{\text{Supernatant protein content} \times \text{supernatant mass}}{\text{Chlorella mass} \times \text{algal powder protein content}} \times 100 \quad [\text{Equation 1}]$$

It should be appreciated that the method of FIG. 2 may also be used to extract soy protein, pea protein, sea buckthorn protein, and other plant proteins from different materials not explicitly listed herein.

Figure 3:
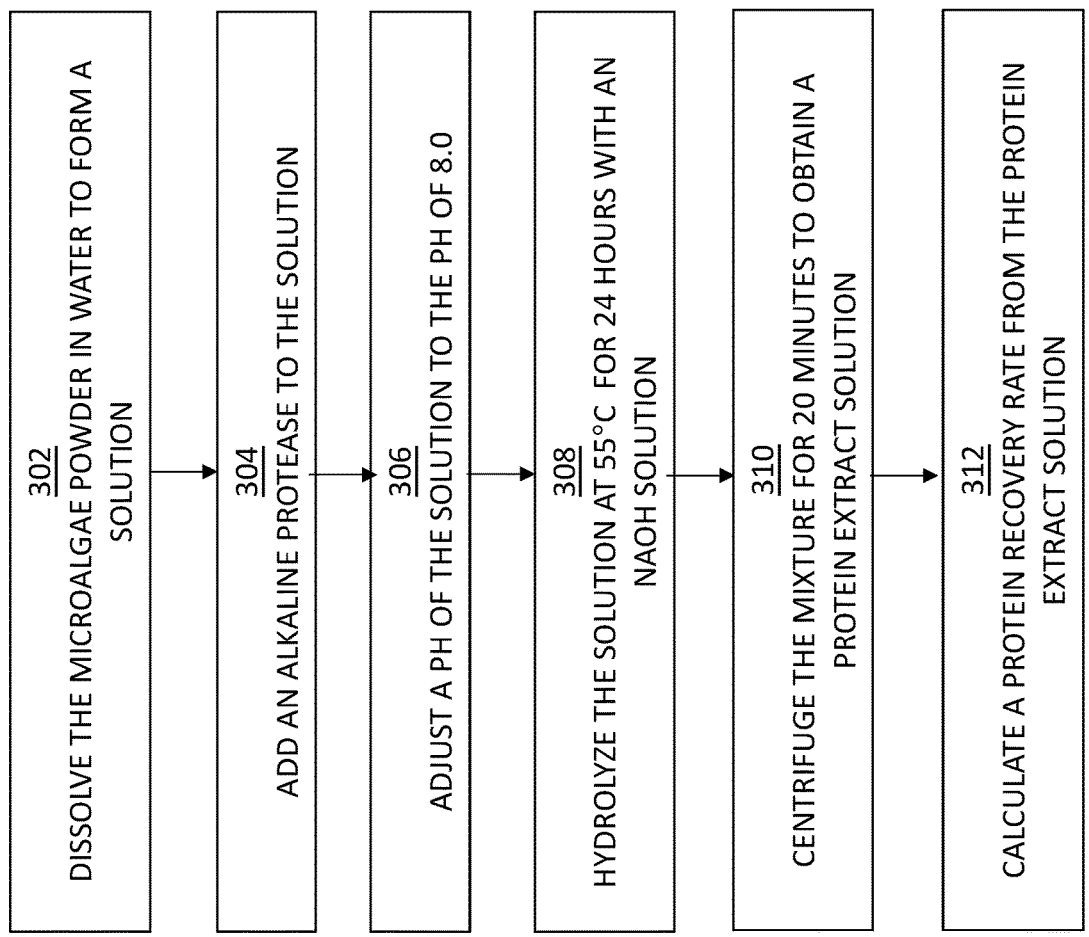
FIG. 3 depicts a schematic block diagram of an enzyme extraction method for *Chlorella* protein, according to at least some embodiments described herein.

FIG. 3 depicts a schematic block diagram of an enzyme extraction method for *Chlorella* protein, according to at least some embodiments described herein. The method of FIG. 3 begins at a process step 302, which includes dissolving approximately 25.0 grams of algae powder in approximately 375 mL of water. The process step 302 is followed by a process step 304, where an alkaline protease is added to the solution. The alkaline protease may be added in an amount between 0.001% to 0.5%. In other examples, the alkaline protease may be added in an amount between 0.01% to 0.2%. In examples, the alkaline protease is cellulase, pectinase, or alkaline protease 37071. However the alkaline protease is not limited to these examples provided herein.

The process step 304 is followed by a process step 306, where a pH of the solution is adjusted to a pH of 8.0. The process step 306 is followed by a process step 308, where the solution is hydrolyzed at 55° C. for approximately 24 hours with the sodium hydroxide solution. The process step 308 is followed by a process step 310, where the solution is centrifuged for approximately 20 minutes to obtain a protein extract solution. The process step 310 is followed by an optional process step 312, where the protein recovery rate is calculated from the protein extract solution via Equation 1. The process step 312 may be followed by additional process steps (not shown) including: extracting the *Chlorella* and drying the *Chlorella*.

Figure 4:
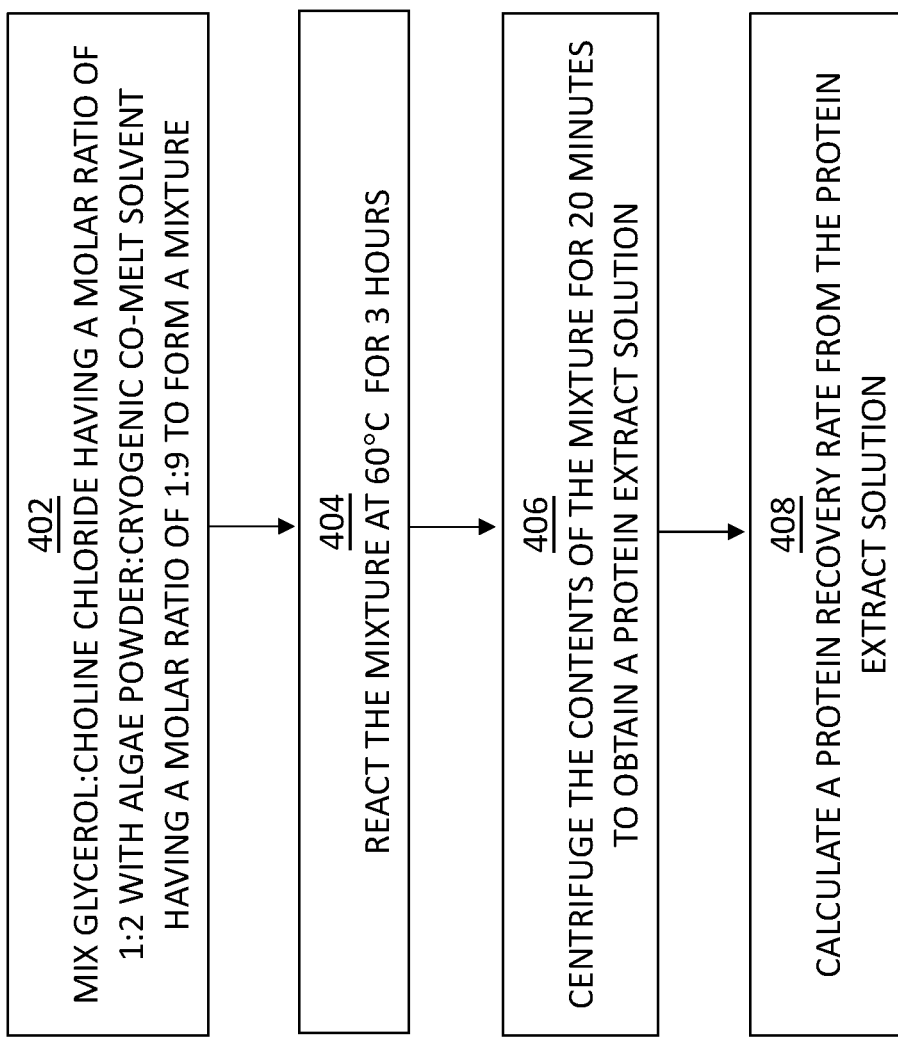
FIG. 4 depicts a schematic block diagram of a first low-temperature deep eutectic solvents (DES) extraction method for *Chlorella* protein, according to at least some embodiments described herein.
Figure 5:
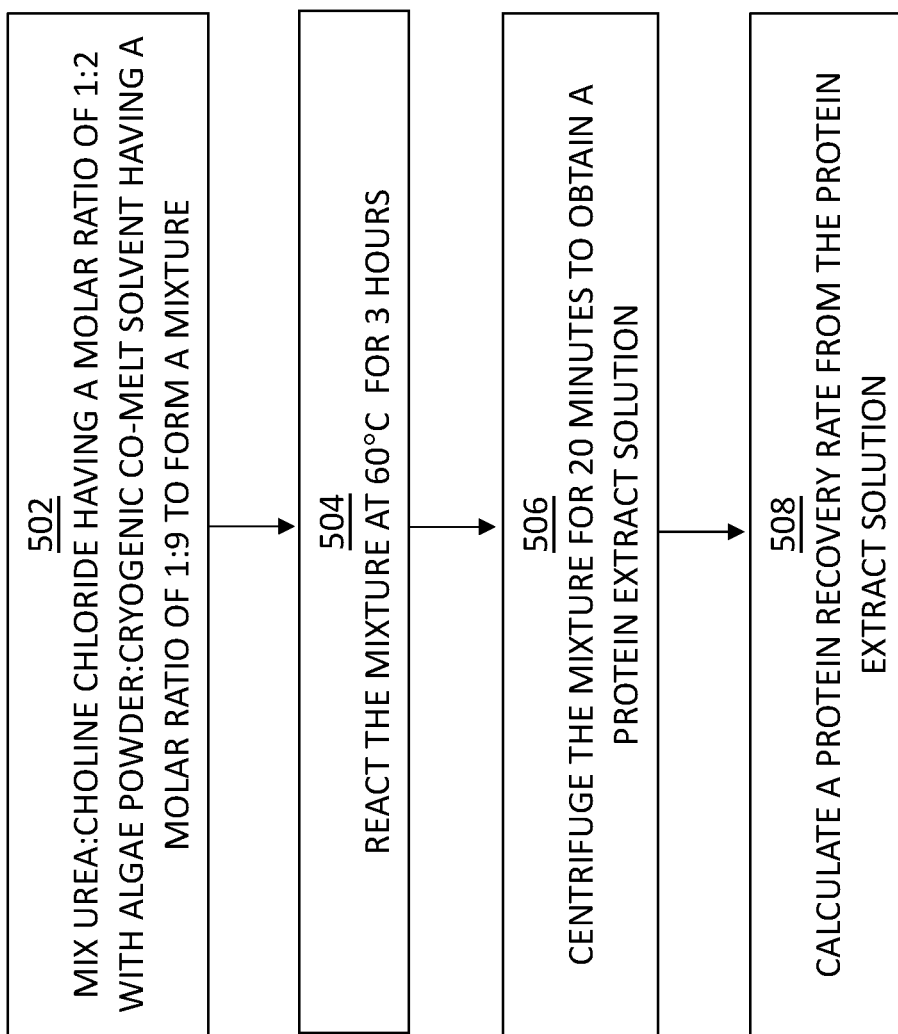
FIG. 5 depicts a schematic block diagram of a second low-temperature DES extraction method for *Chlorella* protein, according to at least some embodiments described herein.

FIG. 4 and FIG. 5 depict schematic block diagrams of a first and a second low-temperature deep eutectic solvent (DES) extraction method for *Chlorella* protein, according to at least some embodiments described herein. DES is a stable solvent formed by the combination of two or three substances by hydrogen bonds between molecules. The composition of DES interacts with a protein (e.g. hydrogen bonding), extracts the protein from raw material, and then separates the protein by washing or alcohol. DES raw materials have a low cost, are easy to biodegrade, and provide better environmental compatibility.

A first method of FIG. 4 begins with a process step 402, which includes mixing a eutectic solvent (e.g., glycerol:choline chloride having a molar ratio of 1:2) with algae powder:cryogenic co-melt solvent having a molar ratio of 1:9. It should be appreciated that other eutectic solvents may be used.

The process step 402 is followed by a process step 404, where the solution is reacted at approximately 60° C. for approximately 3 hours. The process step 404 is followed by a process step 406, where the solution is centrifuged for approximately 20 minutes to obtain a protein extract solution. The process step 406 is followed by an optional process step 408, where the protein recovery rate is calculated from the protein extract solution via the Equation 1.

A second method of FIG. 5 begins with a process step 502, which includes mixing a eutectic solvent (e.g., urea:choline chloride having a molar ratio of 1:2) with algae powder:cryogenic co-melt solvent having a molar ratio of 1:9. The process step 502 is followed by a process step 504, where the solution is reacted at approximately 60° C. for approximately 3 hours. The process step 504 is followed by a process step 506, where the solution is centrifuged for approximately 20 minutes to obtain a protein extract solution. The process step 506 is followed by an optional process step 508, where the protein recovery rate is calculated from the protein extract solution via Equation 1.

When introducing elements of the present disclosure or the embodiments thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A method for making a plant-based food product from a microalgae, the method consisting of:
   extracting a protein from a microalgae by:
   adding an alkaline solution to a powder of the microalgae to form a mixture;
   extracting the protein from the mixture at approximately 50° C. for approximately 6 hours;
   centrifuging the mixture for approximately 20 minutes to obtain a protein extract solution of the protein; and
   calculating a protein recovery rate from the protein extract solution of the protein;
   modifying a culture condition associated with the microalgae to change an amino acid composition of the protein; and
   utilizing the modified protein as a protein flour to create the plant-based food
   product, wherein the plant-based food product is selected from the group consisting of: a meatloaf and a tofu.

2. The method of claim 1, wherein a strain of the microalgae is selected from the group consisting of: a *Botryococcus* strain, a *Neochloris* strain, and a *Chlamydomonas* strain.

3. The method of claim 1, wherein the alkaline solution is added in a range between approximately 1% to approximately 10% of a weight of the protein.

4. The method of claim 1, wherein the algae powder comprises a protein content in a range of approximately 30% to approximately 90%.

5. The method of claim 1, wherein the protein recovery rate of the protein extract solution is calculated by:

$$\text{Protein recovery rate}/\% = \frac{\text{Supernatant protein content} \times \text{supernatant mass}}{\text{Protein mass} \times \text{algal powder protein content}} \times 100.$$

6. The method of claim 1, wherein the alkaline solution is a sodium hydroxide (NaOH) solution.

7. The method of claim 1, wherein the culture condition is
   selected from the group consisting of: a pH level of the microalgae, a wavelength of irradiance of light onto the microalgae during a fermentation process, a feedstock for the microalgae, a carbon source of a culture media, a growth temperature for the
   microalgae, a flow rate of air into a bioreactor during a fermentation process, a flow rate of air/$O_2$ mixtures into the bioreactor during the fermentation process, a flow rate of noble gases into the bioreactor during the fermentation process, and/or an incubation time period for the microalgae under a mixotrophic growth condition.

8. The method of claim 1, further comprising:
   adding a stimulant to a culture media to modify the amino acid
   composition of the *Chlorella* protein.

9. The method of claim 8, wherein:
   the stimulant is a substrate, and
   the substrate is selected from the group consisting of: a spent grain, okara, and
   molasses.

10. The method of claim 4, wherein the algae powder comprises a protein content in a range of approximately 60% to approximately 65%.

* * * * *